United States Patent [19]
Gericke et al.

[11] Patent Number: 5,739,142
[45] Date of Patent: Apr. 14, 1998

[54] 4-AMINOBENZOYLGUANIDINE DERIVATIVES

[75] Inventors: Rolf Gericke, Seeheim-Jugenheim; Manfred Baumgarth, Darmstadt; Norbert Beier, Reinheim; Klaus-Otto Minck, Ober-Ramstadt, all of Germany

[73] Assignee: Merck Patent Gesellschaft Mit Beschrankter Haftung, Darmstadt, Germany

[21] Appl. No.: 592,660

[22] Filed: Jan. 26, 1996

[30] Foreign Application Priority Data

Jan. 28, 1995 [DE] Germany .......... 195 02 644.6

[51] Int. Cl.$^6$ .......... A61K 31/505; A61K 31/425; C07D 239/42; C07D 277/38
[52] U.S. Cl. .......... 514/275; 514/256; 514/331; 514/370; 514/398; 514/399; 514/408; 514/428; 514/603; 514/634; 544/322; 544/332; 546/231; 546/304; 548/196; 548/343.5; 564/85; 564/237
[58] Field of Search .......... 514/256, 275, 514/331, 370, 398, 399, 408, 428, 603, 634; 544/322, 332; 546/231, 304; 564/85, 237; 548/196, 343.5

[56] References Cited

U.S. PATENT DOCUMENTS

| 5,091,394 | 2/1992 | Englert et al. | 514/331 |
| 5,292,755 | 3/1994 | Englert et al. | 514/331 |

FOREIGN PATENT DOCUMENTS

| 2106613 | 3/1994 | Canada |
| 2130944 | 2/1995 | Canada |

Primary Examiner—Yogendra N. Gupta
Attorney, Agent, or Firm—Millen, White, Zelano, & Branigan, P.C.

[57] ABSTRACT

4-Aminobenzoylguanidines of the formula I

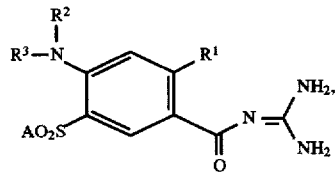

in which A, $R_1$, $R_2$ and $R_3$ have the meanings given, and the physiologically unobjectionable salts thereof exhibit antiarrhythmic properties and are active as inhibitors of the cellular $Na^+/H^+$ antiporter.

20 Claims, No Drawings

4-AMINOBENZOYLGUANIDINE DERIVATIVES

SUMMARY OF THE INVENTION

The invention relates to ortho-substituted 4-aminobenzoylguanidine derivatives of the formula I

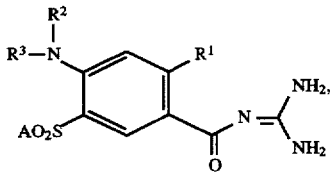

in which $R^1$ is A, $CF_3$, $CH_2F$, $CHF_2$ or $C_2F_5$, $R^2$ and $R^3$ are each independently of one another cycloalkyl having 3 to 7 carbon atoms, Ph or Het, or together, with the nitrogen atom to which they are bonded are an alkylene ring having 4 or 5 carbon atoms, Het is a mono- or dicyclic saturated, unsaturated or aromatic heterocycle having 1 to 4 nitrogen, oxygen and/or sulfur atoms, which heterocycle is attached via N or C, which can be unsubstituted or mono-, di- or trisubstituted by Hal, $CF_3$, A, OH, OA, SH, SA, $NH_2$, NHA, $NA_2$, CN, $NO_2$ and/or carbonyl oxygen, i.e., a carbon atom in the heterocyclic ring can be double bonded to an extra cyclic oxygen atom, A is alkyl having from 1 to 6 carbon atoms, Hal is F, Cl, Br or I, and Ph is unsubstituted phenyl or phenyl which is mono-, di- or trisubstituted by A, OA, $NH_2$, NHA, NA2, F, Cl, Br and/or $CF_3$.

and the physiologically acceptable salts thereof.

An object of the invention was to discover novel compounds having valuable properties, in particular those compounds which can be used for preparing medicaments. It has been found that the compounds of formula I and their physiologically unobjectionable salts possess valuable pharmacological properties while being well tolerated.

The novel compounds are inhibitors of the cellular $Na^+/H^+$ antiporter, i.e. are active compounds which inhibit the cellular $Na^+/H^+$ exchange mechanism (Düsing et al., Med. Klin. 87, 378–384 (1992)) and thus represent good antiarrhythmic agents which are particularly suitable for treating arrhythmias which occur as a result of lack of oxygen.

The best-known active compound of the acylguanidine group is amiloride. However, this substance exhibits primarily a hypotensive and saluretic effect, which is undesirable when treating disturbances of cardiac rhythm, in particular, whereas the antiarrhythmic properties are only very weakly expressed.

In addition to this, structurally similar compounds are known, for example, from EP 04 16 499, equivalent to U.S. Pat. No. 5,091,394 and U.S. Pat. No. 5,292,755.

The invention relates to compounds of the formula I and to physiologically unobjectionable salts thereof.

The novel substances of the present application exhibit a good cardioprotective effect and are therefore particularly suitable for the treatment of infarction, for infarction prophylaxis and for treating angina pectoris. Furthermore, the substances counteract all types of pathological hypoxic and ischaemic damage, so that the disorders which are caused primarily or secondarily by such damage can be treated. The active compounds are also well-suited to preventive applications.

Because of the protective effects of these substances in pathological hypoxic or ischaemic situations, there are further possibilities for using these compounds in association with surgical interventions, for protecting organs which are from time to time less well supplied, in the course of organ transplants, for protecting the organs which are being removed, in association with angioplastic vascular or cardiac interventions, in association with ischaemias of the nervous system, in the therapy of conditions of shock, and for the prophylactic prevention essential hypertension.

In addition, the compounds can also be employed as therapeutic agents in diseases arising from cell proliferation, such as arteriosclerosis, late complications in diabetes, rumour diseases, fibrotic diseases, in particular the lungs, liver and kidneys, and also organ hypertrophies and hyperplasias. Furthermore, the substances are suitable for diagnostic use in order to diagnose diseases which are accompanied by an increased activity of the $Na^+/H^+$ antiporter, for example in erythrocytes, thrombocytes or leucocytes.

All of the compounds of the invention have all of the above effects, to a finite extent. The effects of the compounds can be ascertained using methods which are known per se, as described, for example, by N. Escobales and J. Figueroa in J. Membrane Biol. 120, 41–49 (1991) or by L. Counillon, W. Scholz, H. J. Lang and J. Pouysségur in Mol. Pharmacol. 44, 1041–1045 (1993).

Examples of suitable experimental animals are mice, rats, guinea pigs, dogs, cats, monkeys or pigs.

The compounds can, therefore, be used as pharmaceutical active compounds in human and veterinary medicine. They can also be used as intermediates for preparing further pharmaceutical active compounds.

In the given formulae, A is a branched or unbranched alkyl group having 1–6, preferably 1–4, in particular 1, 2 or 3 carbon atoms, specifically methyl for preference, with ethyl, propyl, isopropyl, butyl and isobutyl also being preferred and sec-butyl, tert-butyl, pentyl, isopentyl (3-methylbutyl), hexyl and isohexyl (4-methylpentyl) being additionally preferred.

$R^1$ is preferably A, especially methyl or ethyl.

$R^2$ and $R^3$ can be identical or different and are preferably, independently of one another, H, A, Phenyl, 2-, 3- or 4-chlorophenyl, 2-, 3- or 4-fluorophenyl or Het. With particular preference, one of the two radicals is hydrogen while the other has one of the preferred meanings mentioned above.

In addition, $R^2$ and $R^3$ can also together be alkylene having 4 or 5 carbon atoms.

If $R^2$ and $R^3$ together are alkylene, then the alkylene group is preferably bulbranched, and specifically is preferably —$(CH_2)_k$— where k is 4 or 5.

Ph is preferably phenyl which is unsubstituted or is monosubstituted by F, Cl, Br, A, OA, $NE_2$, NEA, $NA_2$ or $CF_3$.

Hal is preferably F, Cl or Br.

Het preferably contains 5–7 atoms (including heteroatoms), and is preferably 2- or 3-furyl, 2- or 3-thienyl, 1-, 2- or 3-pyrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, and also preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxidiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl. The heterocyclic radicals can also be partially or completely hydrogenated. Thus Het can also, for example, be 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3 -dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3 -dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3-, -4-, -5- or -6-pyridyl, 1-, 2-, 3- or 4-piperidyl, 2-, 3- or 4-morpholinyl, tetrahydro-2-, -3- or -4-pyranyl, 1,4-dioxanyl, 1,3-dioxane-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl.

It applies generally that all the radicals, for example Het or Ph, which occur two or more times can be identical or different, i.e. are independent of each other.

The invention relates accordingly, in particular, to those compounds of the formula I in which at least one of the said radicals has one of the abovementioned preferred meanings. Some preferred groups of compounds can be expressed by the following formulae Ia to Ii, which correspond to the formula I and in which the radicals which are not more precisely described have the meaning given in the case of the formula I, but in which in Ia $R^1$ is methyl or ethyl;

in Ib $R^1$ is methyl or ethyl and $R^3$ is H;

in Ic $R^1$ is methyl or ethyl, $R^3$ is H and $R^2$ is 2-thiazolyl;

in Id $R^1$ is methyl or ethyl, $R^3$ is H and $R^2$ is imidazolyl or N-methylimidazolyl;

in Ie $R^1$ is methyl or ethyl, $R^3$ is H and $R^2$ is pyridyl or pyrimidinyl;

in If $R^1$ is methyl or ethyl, $R^3$ is H and $R^2$ is phenyl, fluorophenyl or chlorophenyl;

in Ig $R^1$ is methyl or ethyl, $R^3$ is H and $R^2$ is alkyl having 1 to 6 carbon atoms;

in Ih $R^1$ is methyl or ethyl, $R^3$ is H and $R^2$ is piperidyl or pyrrolidinyl;

in Ii $R^1$ is methyl, $R^2$ and $R^3$ are each independently of one another branched or unbranched alkyl having 1 to 6 carbon atoms.

Furthermore, particular preference is given to those compounds which have preferred meanings as cited under Ia to Ih but in which, in addition, —$SO_2A$ is methylsulfonyl and $R^2$ is methyl or ethyl instead of H.

The invention also relates to a process for preparing the compounds of the formula I according to claim 1, and the salts thereof, characterized in that a compound of the formula II

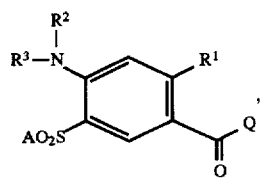

in which $R^1$, $R^2$ $R^3$ and A have the meanings given above and

Q is Cl, Br, OA, O—CO—A, O—CO—Ph, OH or another reactive esterified OH group or a leaving group which can readily be substituted nucleophilically, is reacted with guanidine, or in that a benzoylguanidine of the formula III

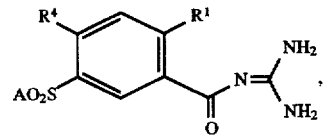

in which $R^1$ and A have the meanings given above and $R^4$ is F, Cl, Br, I or another suitable leaving group, is reacted with an amine or aniline derivative of the formula IV

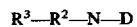

in which $R^2$ and $R^3$ have the meanings given, and D is H, $B(OH)_2$, trialkylsilyl, an alkali metal cation, $NH_4+$ or an easily removable organometallic residue, or in that a compound which otherwise corresponds to the formula I but which contains, instead of one or more hydrogen atoms, one or more reducible groups and/or one or more additional C—C and/or C—N bonds, is treated with a reducing agent, or in that a compound which otherwise corresponds to the formula I but which contains, instead of one or more hydrogen atoms, one or more solvolyzable groups is treated with a solvolyzing agent and/or in that a base of the formula I which is obtained is converted by treatment with an acid into one of its salts.

The compounds of the formula I are otherwise prepared by methods which are known per se, as are described in the literature, (for example in the standard works such as Houben-Weyl, Methoden der organischen Chemie [Methods of organic chemistry], Georg-Thieme-Verlag, Stuttgart; Organic Reactions, John Wiley & Sons, Inc., New York; and in the abovementioned patent application), under reaction conditions which are known and suitable for the reactions mentioned. In this context, use can also be made of variants which are known per se but which have not been mentioned in any more detail.

If desired, the starting compounds can also be formed in situ, such that they are not isolated from the reaction mixture but are instead immediately subjected to further reaction to give the compounds of the formula I.

Preferably, compounds of the formula I are prepared by reacting an activated carboxylic acid derivative of the formula II, where Q is particularly preferably Cl or —O—$CH_3$, with guanidine. Reaction variants are also particularly suitable in which the free carboxylic acid II (Q=OH) is converted, in a manner known per se, into the particular activated derivative which is then directly, without intermediate isolation, reacted with guanidine. Methods in which intermediate isolation can be dispensed with are, for example, activation with carbonyldiimidazol, dicyclohexyl-carbodiimide or the Mukayama variant (Angew. Chem. 91, 788–812 (1979)).

The carboxylic acids of the formula II are prepared, for example, by nucleophilic aromatic substitution starting from appropriate benzoic acid derivatives with corresponding amines. The reaction takes place in analogy to the reaction of compounds III and IV, described below.

The reaction of a reactive carboxylic acid derivative tire of the formula II with guanidine takes place in a manner known per se, preferably in a protic or aprotic polar or apolar inert organic solvent.

Suitable solvents are listed below for the reaction of the compounds III and IV. Particularly preferred solvents, however, are methanol, THF, dimethoxyethane, dioxane, water or mixtures which can be prepared therefrom. Examples of a suitable reaction temperature are temperatures between 20° and the boiling point of the solvent. The reaction times are between 5 minutes and 12 hours. It is expedient to employ an acid scavenger in the reaction. Examples of compounds suitable for this purpose are all types of bases which do not interfere with the reaction itself. It is particularly appropriate, however, to use inorganic bases such as potassium carbonate, or organic bases such as triethylamine or pyridine, or else an excess of guanidine.

Compounds of the formula I according to claim 1 can also be prepared by reacting a benzoylguanidine of the formula III with a compound of the formula IV. The starting compounds of the formula III can be prepared in a simple manner by reacting appropriately substituted benzoic acids or reactive acid derivatives which can be derived therefrom, for example acid halides, esters or anhydrides, with guanidine under reaction conditions as are known per se for the preparation of amides and are generally common. Reaction variants which are particularly suitable in turn are those stated above for the reaction of compound II with guanidine.

The compounds of the formula IV, like the methods for their preparation, are known per se. Where they are not known, they can be prepared by the methods which are known per se.

The preparation of the compound II and the reaction of the compound III with a compound of formula IV take place in a manner which is known per se, preferably in a protic or an aprotic polar inert organic solvent.

A preferred variant, however, involves reacting the reactants directly with one another without adding a solvent.

In the preparation of II or in the reaction of III with IV, it is likewise expedient to work in the presence of a base or with an excess of the basic component. Examples of suitable bases are preferably alkali metal or alkaline earth metal hydroxides, carbonates, or alcoholares or organic bases such as triethylamine or pyridine, which can also be employed in excess and can then serve simultaneously as a solvent.

Suitable inert solvents are, in particular, alcohols, such as methanol, ethanol, isopropanol, n-butanol or tert-butanol; ethers, such as diethyl ether, diisopropyl ether, THF or dioxane; glycol ethers, such as ethylene glycol monomethyl or monoethyl ether (methylglycol or ethylglycol), ethylene glycol dimethyl ether (diglyme); ketones, such as acetone or butanone; nitriles, such as acetonitrile; nitro compounds, such as nitromethane or nitrobenzene; esters, such as ethyl acetate; amides, such as hexamethylphosphoric triamide; sulfoxides, such as dimethyl sulfoxide (DMSO); chlorinated hydrocarbons, such as dichloromethane, chloroform, trichlorethylene, 1,2-dichloroethane or carbon tetrachloride; hydrocarbons, such as benzene, toluene or xylene. Also suitable are mixtures of these solvents with one another.

Furthermore, the compounds of the formula I can be obtained by liberating them from their functional derivatives by solvolysis, especially hydrolysis, or by hydrogenolysis.

Preferred starting compounds for the solvolysis or hydrogenolysis are those which otherwise correspond to the formula I but which contain, instead of one or more free amino and/or hydroxyl groups, corresponding protected amino and/or hydroxyl groups, preferably those which carry, instead of a hydrogen atom which is attached to a nitrogen atom, an amino-protecting group, especially those which carry a group R'—N where R' is an amino-protecting group, instead of an HN group, and/or those which carry, instead of the hydrogen atom of a hydroxyl group, a hydroxy-protecting group, for example those compounds which correspond to the formula I but which carry, instead of an OH group, a group OR" in which R" is a hydroxy-protecting group.

It is also possible for two or more—identical or different—protected amino and/or hydroxyl groups to be present in the molecule of the starting compound. If the protecting groups present are different from one another, then in many cases they can be eliminated selectively.

The term "amino-protecting group" is generally known and relates to groups which are suitable for protecting (blocking) an amino group from chemical reactions, but which can readily be removed after the desired chemical reaction has been carried out at another site in the molecule. Typical of such groups are, in particular, unsubstituted or substituted acyl, aryl (e.g. 2,4-dinitrophenyl (DNP)), aralkoxymethyl (e.g. benzyloxymethyl (BOM)) or aralkyl groups (e.g. benzyl, 4-nitrobenzyl, triphenylmethyl). Since the amino-protecting groups are removed after the desired reaction (or reaction sequence), their type and size is otherwise not critical; however, preference is given to those having 1–20, especially 1–8, carbon atoms. The term "acyl group" in connection with the present process should be interpreted in the widest sense. It embraces acyl groups derived from aliphatic, araliphatic, aromatic or heterocyclic carboxylic or sulfonic acids and also, in particular, alkoxycarbonyl, aryloxycarbonyl and, especially, aralkoxycarbonyl groups. Examples of such acyl groups are alkanoyl such as acetyl, propionyl, butyryl; aralkanoyl such as phenylacetyl; aroyl such as benzoyl or toluoyl; aryloxyalkanoyl such as phenoxyacetyl; alkoxycarbonyl such as methoxycarbonyl, ethoxycarbonyl, 2,2,2-trichloroethoxycarbonyl, isopropoxycarbonyl, tert-butoxycarbonyl (BOC), 2-iodethoxycarbonyl; aralkyloxycarbonyl such as benzyloxycarbonyl (CBZ), 4-methoxybenzyloxycarbonyl, 9-fluoroenylmethoxycarbonyl (FMOC). Preferred amino-protecting groups are BOC, DNP and BOM, and also CBZ, benzyl and acetyl.

The term "hydroxy-protecting group" is likewise generally known and relates to groups which are suitable for protecting a hydroxyl group against chemical reactions but which can readily be removed after the desired chemical reaction has been carried out at another site in the molecule. Typical of such groups are the abovementioned unsubstituted or substituted aryl, aralkyl or acyl groups, and also alkyl groups. The nature and size of the hydroxy-protecting groups is not critical since they are removed again after the desired chemical reaction or reaction sequence; preference is given to groups having 1–20, especially, 1–10, carbon atoms. Examples of hydroxy-protecting groups include tert-butyl, benzyl, p-nitrobenzoyl, p-toluenesulfonyl and acetyl, with benzyl and acetyl being particularly preferred.

The functional derivatives of the compounds of the formula I which are to be used as starting compounds can be prepared by customary methods as described, for example, in the standard works and patent applications mentioned, for example by reacting compounds which correspond to the formulae II and III but where at least one of these compounds contains a protecting group instead of a hydrogen atom.

The liberation of the compounds of the formula I from their functional derivatives is carried out—depending on the protecting group used—with, for example, strong acids, expediently with trifluoroacetic acid or perchloric acid, but also with other strong inorganic acids such as hydrochloric acid or sulfuric acid, strong organic carboxylic acids such as trichloroacetic acid, or sulfonic acid such as benzene-, or p-toluenesulfonic acid. The presence of an additional inert solvent is possible but not always necessary.

Suitable inert solvents are preferably organic, for example carboxylic, acids such as acetic acid, ethers such as tetrahydrofuran (THF) or dioxane, amides such as dimethylformamide (DMF), halogenated hydrocarbons such as dichloromethane, and also alcohols such as methanol, ethanol or isopropanol, and additionally water. Also suitable are mixtures of the abovementioned solvents. Trifluoroacetic acid is preferably used in excess without addition of a further solvent, while perchloric acid is preferably used in the form of a mixture of acetic acid and 70% perchloric acid in a ratio of 9:1. The reaction temperatures for the cleavage are expediently between about 0 and about 50°; it is preferably carried out at between 15° and 30° (room temperature).

The BOC group, for example, can preferably be eliminated with 40% trifluoroacetic acid in dichloromethane or with from about 3 to 5N HCl in dioxane at 15°–60°, while the FMOC group can be eliminated with an approximately 5–20% solution of dimethylamine, diethylamine or piperidine in DMF at 15°–50°. Elimination of the DNP group, for example, is also carried out with an approximately 3–10% solution of 2-mercaptoethanol in DMF/water at 15°–30°.

Protecting groups which can be removed by hydrogenolysis (e.g. BOM, CBZ or benzyl) can be eliminated, for example, by treatment with hydrogen in the presence of a catalyst (for example a noble metal catalyst such as palladium, expediently on a support such as charcoal). Suitable solvents in this context are the solvents mentioned above, particular examples being alcohols such as methanol or ethanol or amides such as DMF. The hydrogenolysis is generally carried out at temperatures between about 0° and 100° and under pressures of between about 1 and 200 bar, preferably at 20°–30° under 1–10 bar. Hydrogenolysis of the CBZ group, for example, takes place satisfactorily over 5–10% Pd/C in methanol at 20°–300.

Furthermore, a base of the formula I can be converted with an acid into the corresponding acid addition salt. Suitable acids for this reaction are those which give physiologically unobjectionable salts. Thus it is possible to use inorganic acids, for example sulfuric acid, nitric acid, hydrohalic acid such as hydrochloric acid or hydrobromic acid, phosphoric acid such as orthophosphoric acid, and sulfamic acid, and also organic acids, especially aliphatic, alicyclic, araliphatic, aromatic or heterocyclic mono- or polybasic carboxylic, sulfonic or sulfuric acids, for example, formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2'- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids, and laurylsulfuric acid.

The compounds of the formula I and their physiologically unobjectionable salts can be used to produce pharmaceutical preparations, especially by a non-chemical route. In this context they can be brought, together with at least one solid, liquid and/or semiliquid excipient or auxiliary and, if appropriate, in combination with one or more additional active compounds, into a suitable dosage form.

The invention additionally relates to compositions, especially pharmaceutical preparations, which comprise at least one compound of the formula I and/or one of its physiologically unobjectionable salts.

These preparations can be used as medicaments in human or veterinary medicines. Suitable excipients are organic or inorganic substances which are suitable for enteral (e.g. oral), parenteral or topical administration, and which do not react with the novel compounds, examples being water, vegetable oils, benzyl alcohols, polyethylene glycols, glycerol triacetate, gelatin, carbohydrates such as lactose or starch, magnesium stearate, talc, tanolin and petroleum jelly. For oral administration use is made, in particular, of tablets, coated tablets, capsules, syrups, juices or drops, for rectal administration of suppositories, for parenteral administration of solutions, preferably oily or aqueous solutions, and also suspensions, emulsions, or implants, for topical application of ointments, creams, pastes, lotions, gels, sprays, foams, aerosols, solutions (for example solutions in alcohols such as ethanol or isopropanol, acetonitrile, DMF, dimethylacetamide, 1,2-propanediol or mixtures thereof with one another and/or with water) or powders. The novel compounds can also be lyophilized and the resulting lyophilizates can be used, for example, to produce preparations for injection.

For topical application in particular, liposomal preparations are also suitable. The preparations indicated can be sterilized and/or can comprise auxiliaries such as glidants, preservatives, stabilizers and/or wetting agents, emulsifiers, salts for influencing the osmotic pressure, buffer substances, colourants, flavourings and/or aroma substances. If desired they can also comprise one or more further active compounds for example one or more vitamins.

The compounds of the formula I and their physiologically unobjectionable salts can be administered to humans or animals, especially mammals such as monkeys, dogs, cats, rats or mice, and can be used for the therapeutic treatment of the human or animal body and also for controlling diseases, in particular in association with the therapy and/or prophylaxis of disturbances in the cardiovascular system. They are therefore suitable for treating arrhythmias, especially when these are induced by lack of oxygen, angina pectoris, infarctions, ischaemias of the nervous system, for example stroke or cerebral oedema, and conditions of shock, and also for preventive treatment.

The substances can also be employed as therapeutic agents in diseases in which cell proliferation plays a role, such as arteriosclerosis, late complications in diabetes, tumour diseases, fibroses and organ hypertrophies and hyperplasias, especially in diseases of the prostate.

In this context, the substances according to the invention are generally administered in analogy to known antiarrhythmics, for example aprindine, preferably in doses of between about 0.01 and 5 mg, in particular between 0.02 and 0.5 mg, per dosage unit. The daily dose is preferably between about 0.0001 and 0.1, in particular between 0.0003 and 0.01, mg/kg of body weight. The specific dosage for each particular patient, however, depends on a wide variety of factors, for example on the activity of the specific compound employed, on the age, on the body weight, on the general state of health, on the sex, on the diet, on the time and route of administration, on the speed of excretion, on the combination of medicines being employed, and on the severity of the particular disease to which the therapy is applied. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application NO. 195 02 644.6, filed Jan. 28, 1995, are hereby incorporated by reference.

In the examples which follow, "worked up in the customary manner" denotes:

Water is added if required and extraction takes place with an organic solvent such as ethyl acetate; the phases are separated, the organic phase is dried over sodium sulfate, filtered and concentrated by evaporation, and the residue is purified by chromatography and/or crystallization.

EXAMPLES

Example 1

6.6 g of 2-ethyl-4-piperidino-5-methylsulfonylbenzoyl chloride [obtainable by reacting 2-ethyl-4-chloro-5-methylsulfonylbenzoic acid with excess piperidine followed by chlorination with $SOCl_2$] dissolved in 60 ml of ethylene glycol dimethyl ether are added dropwise to a solution of 8.7 g of guanidine in 60 ml of ethylene glycol dimethyl ether, and the mixture is stirred at 25° for one hour. 200 ml of ice-water are then added to the reaction mixture, which is acidified with 1N HCl, and subjected twice to extraction with 100 ml of ethyl acetate each time, and the organic phase is discarded. The aqueous phase is rendered alkaline with 1N NaOH and cooled. The product which precipitates is filtered off with suction to give N-diaminomethylene-2-ethyl-4-piperidino-5-methylsulfonylbenzamide, m.p. 218°–220°.

The following compounds are obtained analogously by reacting guanidine with 2-methyl-4-pyrrolidino-5-methylsulfonylbenzoyl chloride:

N-diaminomethylene-2-methyl-4-pyrrolidino-5-methylsulfonylbenzamide, m.p. 222°–224°;

with 2-ethyl-4-pyrrolidino-5-methylsulfonylbenzoyl chloride:

N-diaminomethylene-2-ethyl-4-pyrrolidino-5-methylsulfonylbenzamide;

with 2-methyl-4-N',N'-dimethylamino-5-methylsulfonylbenzoyl chloride:

N-diaminomethylene-2-methyl-4-N',N'-dimethylamino-5-methylsulfonylbenzamide;

with 2-ethyl-4-N',N'-diethylamino-5-methylsulfonylbenzoyl chloride:

N-diaminomethylene-2-ethyl-4-N',N'-diethylamino-5-methylsulfonylbenzamide;

with 2-ethyl-4-N',N'-dimethylamino-5-methylsulfonylbenzoyl chloride:

N-diaminomethylene-2-ethyl-4-N',N'-dimethylamino-5-methylsulfonylbenzamide;

with 2-methyl-4-N',N'-diethylamino-5-methylsulfonylbenzoyl chloride:

N-diaminomethylene-2-methyl-4-N',N'-diethylamino-5-methylsulfonylbenzamide.

Example 2

4 g of N-diaminomethylene-2-ethyl-4-piperidino-5-methylsulfonylbenzamide [obtainable according to Example 1] are suspended in 100 ml of water, dissolved with the stoichiometric quantity of 1-molar aqueous HCl solution and then freeze-dried to give N-diaminomethylene-2-ethyl-4-piperidino-5-methylsulfonylbenzamide, hydrochloride, m.p.>250°.

The following compounds are obtained analogously by treatment with aqueous HCl followed by freeze-drying:

from N-diammnomethylene-2-methyl-4-pyrrolidino-5-methylsulfonylbenzamide:

N-diaminomethylene-2-methyl-4-pyrrolidino-5-methylsulfonylbenzamide, hydrochloride;

from N-diaminomethylene-2-ethyl-4-pyrrolidino-5-methylsulfonylbenzamide:

N-diaminomethylene-2-ethyl-4-pyrrolidino-5-methylsulfonylbenzamide, hydrochloride;

from N-diaminomethylene-2-methyl-4-phenylamino-5-methylsulfonylbenzamide:

N-diaminomethylene-2-methyl-4-phenylamino-5-methylsulfonylbenzamide, hydrochloride, m.p.>260°.

Example 3

A solution of 20 g of methyl 2-methyl-4-piperidino-5-methylsulfonylbenzoate [obtainable by reacting piperidine with 2-methyl-4-chloro-5-methylsulfonylbenzoic acid followed by esterification] and 30 g of guanidine, which has been liberated beforehand from the guanadine hydrochloride using sodium methylate, is stirred in 160 ml of methanol at 50° over a period of twenty hours. After cooling to 0°, water is added, stirring is continued for 1 hour and the precipitate which forms is separated off. Recrystallization from dichloromethane/methanol gives N-diaminomethylene-2-methyl-4-piperidino-5-methylsulfonylbenzamide, m.p. 222°–224°, hydrochloride m.p. 275°–276°.

Example 4

2.1 g of N-diaminomethylene-2-methyl-4-piperidino-5-methylsulfonylbenzamide [obtainable according to Example 3] are treated for 1 hour with 1-molar aqueous HCl solution and then freeze-dried, to give N-diaminomethylene-2-methyl-4-piperidino-5-methylsulfonylbenzamide, dihydrochloride, m.p. 247°.

Example 5

1 g of N-diaminomethylene-2-methyl-4-chloro-5-methylsulfonylbenzamide [obtainable by reacting 2-methyl-4-chloro-5-methylsulfonylbenzoyl chloride with guanidine according to Example 1], 1 g of diisopropylamine, 1 ml of Sulfolan® and 0.55 g of potassium carbonate are combined and the mixture is stirred at 110° for seven hours. 50 ml of ethyl acetate are then added and the reaction mixture is subjected to extraction with 50 ml of 1N HCl. The aqueous phase is adjusted to a pH of 12 with 1N NaOH and subjected twice to extraction with 100 ml of ethyl acetate each time. After the mixture has been worked up in the customary manner, recrystallization from acetone gives N-diaminomethylene-2-methyl-4-(N',N'-diisopropylamino)-5-methylsulfonylbenzamide.

The following compound is obtained analogously by reacting N-diaminomethylene-2-methyl-4-chloro-5-methylsulfonylbenzamide with dipropylamine:

N-diaminomethylene-2-methyl-4-(N',N'-dipropylamino)-5-methylsulfonylbenzamide.

Example 6

The following compounds are obtained in analogy to Example 1 by reacting guanidine with 2-methyl-4-phenylamino-5-methylsulfonylbenzoyl chloride:
N-diaminomethylene-2-methyl-4-phenylamino-5-methylsulfonylbenzamide, m.p. 202°–207°;

with 2-methyl-4-N-methylanilino-5-methylsulfonylbenzoyl chloride:
N-diaminomethylene-2-methyl-4-N-methylanilino-5-methylsulfonylbenzamide;

with 2-methyl-4-diphenylamino-5-methylsulfonylbenzoyl chloride:
N-diaminomethylene-2-methyl-4-diphenylamino-5-methylsulfonylbenzamide;

with 2-ethyl-4-diphenylamino-5-methylsulfonylbenzoyl chloride:
N-diaminomethylene-2-ethyl-4-diphenylamino-5-methylsulfonylbenzamide;

with 2-methyl-4-(2-chlorophenylamino)-5-methylsulfonylbenzoyl chloride:
N-diaminomethylene-2-methyl-4-(2-chlorophenylamino)-5-methylsulfonylbenzamide;

with 2-methyl-4-(N-methyl-2-chlorophenylamino)-5-methylsulfonylbenzoyl chloride:
N-diaminomethylene-2-methyl-4-(N-methyl-2-chloroanilino)-5-methylsulfonylbenzamide;

with 2-methyl-4-(3-chlorophenylamino)-5-methylsulfonylbenzoyl chloride:
N-diaminomethylene-2-methyl-4-(3-chlorophenylamino)-5-methylsulfonylbenzamide, m.p. 193°–197°; m.p. 234°–237° (methanesulfonate);

with 2-methyl-4-(N-methyl-3-chloroanilino)-5-methylsulfonylbenzoyl chloride:
N-diaminomethylene-2-methyl-4-(N-methyl-3-chloroanilino)-5-methylsulfonylbenzamide;

with 2-methyl-4-(4-chlorophenylamino)-5-methylsulfonylbenzoyl chloride:
N-diaminomethylene-2-methyl-4-(4-chlorophenylamino)-5-methylsulfonylbenzamide;

with 2-methyl-4-(N-methyl-4-chloroanilino)-5-methylsulfonylbenzoyl chloride:
N-diaminomethylene-2-methyl-4-(N-methyl-4-chloroanilino)-5-methylsulfonylbenzamide;

with 2-methyl-4-(2-fluorophenylamino)-5-methylsulfonylbenzoyl chloride:
N-diaminomethylene-2-methyl-4-(2-fluorophenylamino)-5-methylsulfonylbenzamide;

with 2-methyl-4-(N-methyl-2-fluoroanilino)-5-methylsulfonylbenzoyl chloride:
N-diaminomethylene-2-methyl-4-(N-methyl-2-fluoroanilino)-5-methylsulfonylbenzamide;

with 2-methyl-4-(3-fluorophenylamino)-5-methylsulfonylbenzoyl chloride:
N-diaminomethylene-2-methyl-4-(3-fluorophenylamino)-5-methylsulfonylbenzamide;

with 2-methyl-4-(N-methyl-3-fluoroanilino)-5-methylsulfonylbenzoyl chloride:
N-diaminomethylene-2-methyl-4-(N-methyl-3-fluoroanilino)-5-methylsulfonylbenzamide;

with 2-methyl-4-(4-fluorophenylamino)-5-methylsulfonylbenzoyl chloride:
N-diaminomethylene-2-methyl-4-(4-fluorophenylamino)-5-methylsulfonylbenzamide;

with 2-methyl-4-(N-methyl-4-fluoroanilino)-5-methylsulfonylbenzoyl chloride:
N-diaminomethylene-2-methyl-4-(N-methyl-4-fluoroanilino)-5-methylsulfonylbenzamide;

with 2-methyl-4-(2-methoxyphenylamino)-5-methylsulfonylbenzoyl chloride:
N-diaminomethylene-2-methyl-4-(2-methoxyphenylamino)-5-methylsulfonylbenzamide;

with 2-methyl-4-(N-methyl-2-methoxyanilino)-5-methylsulfonylbenzoyl chloride:
N-diaminomethylene-2-methyl-4-(N-methyl-2-methoxyanilino)-5-methylsulfonylbenzamide;

with 2-methyl-4-(3-methoxyphenylamino)-5-methylsulfonylbenzoyl chloride:
N-diaminomethylene-2-methyl-4-(3-methoxyphenylamino)-5-methylsulfonylbenzamide;

with 2-methyl-4-(N-methyl-3-methoxyanilino)-5-methylsulfonylbenzoyl chloride:
N-diaminomethylene-2-methyl-4-(N-methyl-3-methoxyanilino)-5-methylsulfonylbenzamide;

with 2-methyl-4-(4-methoxyphenylamino)-5-methylsulfonylbenzoyl chloride:
N-diaminomethylene-2-methyl-4-(4-methoxyphenylamino)-5-methylsulfonylbenzamide;

with 2-methyl-4-(N-methyl-4-methoxyanilino)-5-methylsulfonylbenzoyl chloride:
N-diaminomethylene-2-methyl-4-(N-methyl-4-methoxyanilino)-5-methylsulfonylbenzamide;

with 2-methyl-4-(2-cyanophenylamino)-5-methylsulfonylbenzoyl chloride:
N-diaminomethylene-2-methyl-4-(2-cyanophenylamino)-5-methylsulfonylbenzamide;

with 2-methyl-4-(N-methyl-2-cyanoanilino)-5-methylsulfonylbenzoyl chloride:
N-diaminomethylene-2-methyl-4-(N-methyl-2-cyanoanilino)-5-methylsulfonylbenzamide;

with 2-methyl-4-(3-cyanophenylamino)-5-methylsulfonylbenzoyl chloride:
N-diaminomethylene-2-methyl-4-(3-cyanophenylamino)-5-methylsulfonylbenzamide;

with 2-methyl-4-(N-methyl-3-cyanoanilino)-5-methylsulfonylbenzoyl chloride:
N-diaminomethylene-2-methyl-4-(N-methyl-3-cyanoanilino)-5-methylsulfonylbenzamide;

with 2-methyl-4-(4-cyanophenylamino)-5-methylsulfonylbenzoyl chloride:
N-diaminomethylene-2-methyl-4-(4-cyanophenylamino)-5-methylsulfonylbenzamide;

with 2-methyl-4-(N-methyl-4-cyanophenylamino)-5-methylsulfonylbenzoyl chloride:
N-diaminomethylene-2-methyl-4-(N-methyl-4-cyanoanilino)-5-methylsulfonylbenzamide;

with 2-methyl-4-(2-trifluoromethylphenylamino)-5-methylsulfonylbenzoyl chloride:
N-diaminomethylene-2-methyl-4-(2-trifluoromethylphenylamino)-5-methylsulfonylbenzamide;

with 2-methyl-4-(N-methyl-2-trifluoromethylanilino)-5-methylsulfonylbenzoyl chloride:

N-diaminomethylene-2-methyl-4-(N-methyl-2-trifluoromethylanilino)-5-methylsulfonylbenzamide;

with 2-methyl-4-(3-trifluoromethylphenylamino)-5-methylsulfonylbenzoyl chloride:

N-diaminomethylene-2-methyl-4-(3-trifluoromethylphenylamino)-5-methylsulfonylbenzamide;

with 2-methyl-4-(4-trifluoromethylphenylamino)-5-methylsulfonylbenzoyl chloride:

N-diaminomethylene-2-methyl-4-(4-trifluoromethylphenylamino)-5-methylsulfonylbenzamide;

with 2-methyl-4-(N-methyl-4-trifluoromethylanilino)-5-methylsulfonylbenzoyl chloride:

N-diaminomethylene-2-methyl-4-(N-methyl-4-trifluoromethylanilino)-5-methylsulfonylbenzamide.

The following compounds are obtained analogously by reacting guanidine.

with 2-ethyl-4-(N',N'-diisopropylamino)-5-methylsulfonylbenzoyl chloride:

N-diaminomethylene-2-ethyl-4-(N',N'-diisopropylamino)-5-methylsulfonylbenzamide;

with 2-ethyl-4-(N',N'-dipropylamino)-5-methylsulfonylbenzoyl chloride:

N-diaminomethylene-2-ethyl-4-(N',N'-dipropylamino)-5-methylsulfonylbenzamide;

with 2-ethyl-4-phenylamino-5-methylsulfonylbenzoyl chloride:

N-diaminomethylene-2-ethyl-4-phenylamino-5-methylsulfonylbenzamide;

with 2-ethyl-4-N-methylanilino-5-methylsulfonylbenzoyl chloride:

N-diaminomethylene-2-ethyl-4-N-methylanilino-5-methylsulfonylbenzamide;

with 2-ethyl-4-(2-chlorophenylamino)-5-methylsulfonylbenzoyl chloride:

N-diaminomethylene-2-ethyl-4-(2-chlorophenylamino)-5-methylsulfonylbenzamide;

with 2-ethyl-4-(N-methyl-2-chloroanilino)-5-methylsulfonylbenzoyl chloride:

N-diaminomethylene-2-ethyl-4-(N-methyl-2-chloroanilino)-5-methylsulfonylbenzamide;

with 2-ethyl-4-(3-chlorophenylamino)-5-methylsulfonylbenzoyl chloride:

N-diaminomethylene-2-ethyl-4-(3-chlorophenylamino)-5-methylsulfonylbenzamide;

with 2-ethyl-4-(N-methyl-3-chloroanilino)-5-methylsulfonylbenzoyl chloride:

N-diaminomethylene-2-ethyl-4-(N-methyl-3-chloroanilino)-5-methylsulfonylbenzamide;

with 2-ethyl-4-(4-chlorophenylamino)-5-methylsulfonylbenzoyl chloride:

N-diaminomethylene-2-ethyl-4-(4-chlorophenylamino)-5-methylsulfonylbenzamide;

with 2-ethyl-4-(N-methyl-4-chloroanilino)-5-methylsulfonylbenzoyl chloride:

N-diaminomethylene-2-ethyl-4-(N-methyl-4-chloroanilino)-5-methylsulfonylbenzamide;

with 2-ethyl-4-(2-fluorophenylamino)-5-methylsulfonylbenzoyl chloride:

N-diaminomethylene-2-ethyl-4-(2-fluorophenylamino)-5-methylsulfonylbenzamide;

with 2-ethyl-4-(N-methyl-2-fluoroanilino)-5-methylsulfonylbenzoyl chloride:

N-diaminomethylene-2-ethyl-4-(N-methyl-2-fluoroanilino)-5-methylsulfonylbenzamide;

with 2-ethyl-4-(3-fluorophenylamino)-5-methylsulfonylbenzoyl chloride:

N-diaminomethylene-2-ethyl-4-(3-fluorophenylamino)-5-methylsulfonylbenzamide;

with 2-ethyl-4-(N-methyl-3-fluoroanilino)-5-methylsulfonylbenzoyl chloride:

N-diaminomethylene-2-ethyl-4-(N-methyl-3-fluoroanilino)-5-methylsulfonylbenzamide;

with 2-ethyl-4-(4-fluorophenylamino)-5-methylsulfonylbenzoyl chloride:

N-diaminomethylene-2-ethyl-4-(4-fluorophenylamino)-5-methylsulfonylbenzamide;

with 2-ethyl-4-(N-methyl-4-fluoroanilino)-5-methylsulfonylbenzoyl chloride:

N-diaminomethylene-2-ethyl-4-(N-methyl-4-fluoroanilino)-5-methylsulfonylbenzamide;

with 2-ethyl-4-(2-methoxyphenylamino)-5-methylsulfonylbenzoyl chloride:

N-diaminomethylene-2-ethyl-4-(2-methoxyphenylamino)-5-methylsulfonylbenzamide;

with 2-ethyl-4-(N-methyl-2-methoxyanilino)-5-methylsulfonylbenzoyl chloride:

N-diaminomethylene-2-ethyl-4-(N-methyl-2-methoxyanilino)-5-methylsulfonylbenzamide;

with 2-ethyl-4-(3-methoxyphenylamino)-5-methylsulfonylbenzoyl chloride:

N-diaminomethylene-2-ethyl-4-(3-methoxyphenylamino)-5-methylsulfonylbenzamide;

with 2-ethyl-4-(N-methyl-3-methoxyanilino)-5-methylsulfonylbenzoyl chloride:

N-diaminomethylene-2-ethyl-4-(N-methyl-3-methoxyanilino)-5-methylsulfonylbenzamide;

with 2-ethyl-4-(4-methoxyphenylamino)-5-methylsulfonylbenzoyl chloride:

N-diaminomethylene-2-ethyl-4-(4-methoxyphenylamino)-5-methylsulfonylbenzamide;

with 2-ethyl-4-(N-methyl-4-methoxyanilino)-5-methylsulfonylbenzoyl chloride:

N-diaminomethylene-2-ethyl-4-(N-methyl-4-methoxyanilino)-5-methylsulfonylbenzamide;

with 2-ethyl-4-(2-cyanophenylamino)-5-methylsulfonylbenzoyl chloride:

N-diaminomethylene-2-ethyl-4-(2-cyanophenylamino)-5-methylsulfonylbenzamide;

with 2-ethyl-4-(N-methyl-2-cyanoanilino)-5-methylsulfonylbenzoyl chloride:

N-diaminomethylene-2-ethyl-4-(N-methyl-2-cyanoanilino)-5-methylsulfonylbenzamide;

with 2-ethyl-4-(3-cyanophenylamino)-5-methylsulfonylbenzoyl chloride:

N-diaminomethylene-2-ethyl-4-(3-cyanophenylamino)-5-methylsulfonylbenzamide;

with 2-ethyl-4-(N-methyl-3-cyanoanilino)-5-methylsulfonylbenzoyl chloride:

N-diaminomethylene-2-ethyl-4-(N-methyl-3-cyanoanilino)-5-methylsulfonylbenzamide;

with 2-ethyl-4-(4-cyanophenylamino)-5-methylsulfonylbenzoyl chloride:

N-diaminomethylene-2-ethyl-4-(4-cyanophenylamino)-5-methylsulfonylbenzamide;

with 2-ethyl-4(N-methyl-4-cyanoanilino)-5-methylsulfonylbenzoyl chloride:

N-diaminomethylene-2-ethyl-4-(N-methyl-4-cyanoanilino)-5-methylsulfonylbenzamide;

with 2-ethyl-4-(2-trifluoromethylphenylamino)-5-methylsulfonylbenzoyl chloride:

N-diaminomethylene-2-ethyl-4-(2-trifluoromethylphenylamino)-5-methylsulfonylbenzamide;

with 2-ethyl-4-(N-methyl-2-trifluoromethylanilino)-5-methylsulfonylbenzoyl chloride:

N-diaminomethylene-2-ethyl-4-(N-methyl-2-trifluoromethylanilino)-5-methylsulfonylbenzamide;

with 2-ethyl-4-(3'-trifluoromethylphenylamino)-5-methylsulfonylbenzoyl chloride:

N-diaminomethylene-2-ethyl-4-(3-trifluoromethylphenylamino)-5-methylsulfonylbenzamide;

with 2-ethyl-4-(4-trifluoromethylphenylamino)-5-methylsulfonylbenzoyl chloride:

N-diaminomethylene-2-ethyl-4-(4-trifluoromethylphenylamino)-5-methylsulfonylbenzimide;

with 2-ethyl-4-(N-methyl-4-trifluoromethylphenylanilino)-5-methylsulfonylbenzoyl chloride:

N-diaminomethylene-2-ethyl-4-(N-methyl-4-trifluoromethylanilino)-5-methylsulfonylbenzamide.

Example 7

A procedure analogous to Example 1, which involves reacting gaunidine with 2-methyl-4-(2-pyridylamino)-5-methylsulfonylbenzoyl chloride [obtainable by reacting 2-methyl-4-fluoro-5-methylsulfonylbenzoic acid with 2-aminopyridine followed by conversion to the acid chloride with SOCl₂] give N-diaminomethylene-2-methyl-4-(2-pyridylamino)-5-methylsulfonylbenzamide, m.p. 225°–226°; m.p. 235°–237° (methanesulfonate).

The following compounds are obtained analogously by reacting guanidine with 2-methyl-4-(3-pyridylamino)-5-methylsulfonylbenzoyl chloride:

N-diaminomethylene-2-methyl-4-(3-pyridylamino)-5-methylsulfonylbenzamide;

with 2-methyl-4-(3-pyridyl-N-methylamino)-5-methylsulfonylbenzoyl chloride:

N-diaminomethylene-2-methyl-4-(3-pyridyl-N-methylamino)-5-methylsulfonylbenzamide;

with 2-methyl-4-(2-pyridyl-N-methylamino)-5-methylsulfonylbenzoyl chloride:

N-diaminomethylene-2-methyl-4-(2-pyridyl-N-methylamino)-5-methylsulfonylbenzamide;

with 2-methyl-4-(4-pyridylamino)-5-methylsulfonylbenzoyl chloride:

N-diaminomethylene-2-methyl-4-(4-pyridylamino)-5-methylsulfonylbenzamide, m.p. 247°–248°, m.p. 243°–245° (methanesulfonate);

with 2-methyl-4-(4-pyridyl-N-methylamino)-5-methylsulfonylbenzoyl chloride:

N-diaminomethylene-2-methyl-4-(4-pyridyl-N-methylamino)-5-methylsulfonylbenzamide;

with 2-methyl-4-(2-pyrimidinylamino)-5-methylsulfonylbenzoyl chloride:

N-diaminomethylene-2-methyl-4-(2-pyrimidinylamino)-5-methylsulfonylbenzamide;

with 2-methyl-4-(2-pyrimidinyl-N-methylamino)-5-methylsulfonylbenzoyl chloride:

N-diaminomethylene-2-methyl-4-(2-pyrimidinyl-N-methylamino)-5-methylsulfonylbenzamide;

with 2-methyl-4-(1-methylimidazolyl-2-amino)-5-methylsulfonylbenzoyl chloride:

N-diaminomethylene-2-methyl-4-(1-methylimidazolyl-2-amino)-5-methylsulfonylbenzamide;

with 2-methyl-4-(1-methylimidazolyl-2-N-methylamino)-5-methylsulfonylbenzoyl chloride:

N-diaminomethylene-2-methyl-4-(1-methylimidazolyl-2-N-methylamino)-5-methylsulfonylbenzamide;

with 2-methyl-4-(2-thiazolylamino)-5-methylsulfonylbenzoyl chloride:

N-diaminomethylene-2-methyl-4-(2-thiazolylamino)-5-methylsulfonylbenzamide;

with 2-methyl-4-(2-thiazolyl-N-methylamino)-5-methylsulfonylbenzoyl chloride:

N-diaminomethylene-2-methyl-4-(2-thiazolyl-N-methylamino)-5-methylsulfonylbenzamide;

with 2-ethyl-4-(2-pyridylamino)-5-methylsulfonylbenzoyl chloride:

N-diaminomethylene-2-ethyl-4-(2-pyridylamino)-5-methylsulfonylbenzamide;

with 2-ethyl-4-(3-pyridylamino)-5-methylsulfonylbenzoyl chloride:

N-diaminomethylene-2-ethyl-4-(3-pyridylamino)-5-methylsulfonylbenzamide;

with 2-ethyl-4-(3-pyridyl-N-methylamino)-5-methylsulfonylbenzoyl chloride:

N-diaminomethylene-2-ethyl-4-(3-pyridyl-N-methylamino)-5-methylsulfonylbenzamide;

with 2-ethyl-4-(2-pyridyl-N-methylamino)-5-methylsulfonylbenzoyl chloride:

N-diaminomethylene-2-ethyl-4-(2-pyridyl-N-methylamino)-5-methylsulfonylbenzamide;

with 2-ethyl-4-(4-pyridylamino)-5-methylsulfonylbenzoyl chloride:

N-diaminomethylene-2-ethyl-4(4-pyridylamino)-5-methylsulfonylbenzamide;

with 2-ethyl-4-(4-pyridyl-N-methylamino)-5-methylsulfonylbenzoyl chloride:

N-diaminomethylene-2-ethyl-4-(4-pyridyl-N-methylamino)-5-methylsulfonylbenzamide;

with 2-ethyl-4-(2-pyrimidinylamino)-5-methylsulfonylbenzoyl chloride:

N-diaminomethylene-2-ethyl-4-(2-pyrimidinylamino)-5-methylsulfonylbenzamide;

with 2-ethyl-4-(2-pyrimidinyl-N-methylamino)-5-methylsulfonylbenzoyl chloride:

N-diaminomethylene-2-ethyl-4-(2-pyrimidinyl-N-methylamino)-5-methylsulfonylbenzamide;

with 2-ethyl-4-(1-methylimidazolyl-2-amino)-5-methylsulfonylbenzoyl chloride:

N-diaminomethylene-2-ethyl-4-(1-methylimidazolyl-2-amino)-5-methylsulfonylbenzamide;

with 2-ethyl-4-(1-methylimidazolyl-2-N-methylamino)-5-methylsulfonylbenzoyl chloride:

N-diaminomethylene-2-ethyl-4-(1-methylimidazolyl-2-N-methylamino)-5-methylsulfonylbenzamide;

with 2-ethyl-4-(2-thiazolylamino)-5-methylsulfonylbenzoyl chloride:

N-diaminomethylene-2-ethyl-4-(2-thiazolylamino)-5-methylsulfonylbenzamide;

with 2-ethyl-4-(2-thiazolyl-N-methylamino)-5-methylsulfonylbenzoyl chloride:

N-diaminomethylene-2-ethyl-4-(2-thiazolyl-N-methylamino)-5-methylsulfonylbenzamide.

The examples which follow relate to pharmaceutical preparations:

Example A

Injection Vials

A solution of 100 g of an active compound of the formula I and 5 g of disodium hydrogen phosphate in 3 l of double-distilled water is adjusted to a pH of 6.5 using 2N hydrochloric acid, sterilized by filtration and dispersed into injection vials, which are then lyophilized under sterile conditions and sealed in a sterile manner. Each injection vial contains 5 mg of active compound.

Example B

Suppositories

A mixture of 20 g of an active compound of the formula I is melted with 100 of soya lecithin and 1400 g of cocoa butter, poured into moulds and allowed to cool. Each suppository contains 20 mg of active compound.

Example C

Solution

A solution is prepared from 1 g of an active compound of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of double-distilled water. The solution is adjusted to a pH of 6.8, made up to 1 l and sterilized by irradiation. This solution can be used in the form of eyedrops.

Example D

Ointment 500 mg of an active compound of the formula I are mixed with 99.5 g of petroleum jelly under aseptic conditions.

Example E

Tablets

A mixture of 1 kg of active compound of the formula I, 4 kg of lactose, 1.2 kg of potato starch, 0.2 kg of talc and 0.1 kg of magnesium stearate is pressed in a customary manner to give tablets such that each tablet contains 10 mg of active compound.

Example F

Coated Tablets

In analogy to Example E, tablets are pressed which are subsequently coated in a customary manner with a coating comprising sucrose, potato starch, talc, tragacanth and colourant.

Example G

Capsules

Hard gelatin capsules are filled in a customary manner with 2 kg of active compound of the formula I such that each capsule contains 20 mg of the active compound.

Example H

Ampoules

A solution of 1 kg of active compound of the formula I in 60 l of double-distilled water is sterilized by filtration and dispensed into ampoules, which are lyophilized under sterile conditions and sealed in a sterile manner. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A 4-aminobenzoylguanidine of formula I

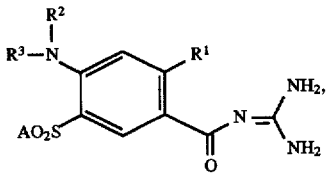

in which $R^1$ is A, $CF_3$, $CH_2F$, $CHF_2$ or $C_2F_5$, $R^2$ and $R^3$ are each independently H, A, $C_{3-7}$-cycloalkyl, Ph or Het, or together with the nitrogen atom to which they are bonded are a $C_{4-5}$ alkylene ring, Het: is a mono- or dicyclic saturated, unsaturated or aromatic heterocycle having 1 to 4 nitrogen, oxygen and/or sulfur atoms, which heterocycle is attached via N or C, which can be unsubstituted or mono-, di- or trisubstituted by Hal, $CF_3$, A, OH, OA, SH, SA, $NH_2$, NHA, $NA_2$, CN, $NO_2$ and/or carbonyl oxygen, A is $C_{1-6}$-alkyl, Hal is F, Cl, Br or I, and Ph is unsubstituted phenyl or phenyl which is mono-, di- or trisubstituted by A, OA, $NH_2$, NHA, $NA_2$, F, Cl, Br and/or $CF_3$, or a physiologically acceptable salt thereof.

2. A compound according to claim 1, wherein $R^1$ is methyl or ethyl.

3. A compound according to claim 1, wherein $R^1$ is methyl or ethyl and $R^3$ is H.

4. A compound according to claim 1, wherein $R^1$ is methyl or ethyl, $R^3$ is H and $R^2$ is 2-thiazolyl.

5. A compound according to claim 1, wherein $R^1$ is methyl or ethyl, $R^3$ is H and $R^2$ is imidazolyl or N-methylimidazolyl.

6. A compound according to claim 1, wherein $R^1$ is methyl or ethyl, $R^3$ is H and $R^2$ is pyridyl or pyrimidinyl.

7. A compound according to claim 1, wherein $R^1$ is methyl or ethyl, $R^3$ is H and $R^2$ is phenyl, fluorophenyl or chlorophenyl.

8. A compound according to claim 1, wherein $R^1$ is methyl or ethyl, $R^3$ is H and $R^2$ is alkyl having 1 to 6 carbon atoms.

9. A compound according to claim 1, wherein $R^1$ is methyl or ethyl, $R^3$ is H and $R^2$ is piperidyl or pyrrolidinyl.

10. A compound according to claim 1, wherein $R^1$ is methyl, $R^2$ and $R^3$ are each independently of one another branched or unbranched alkyl having 1 to 6 carbon atoms.

11. A compound according to claim 1, wherein $R^2$ is methyl or ethyl and A is methyl.

12. A compound according to claim 1, which is (a) diaminomethylene-2-ethyl-4-piperidino-5-methylsulfonylbenzamide;

(b) N-diaminomethylene-2-methyl-4-piperidino-5-methylsulfonylbenzamide;

(c) N-diaminomethylene-2-methyl-4-(N', N'-diisopropylamino)-5-methylsulfonylbenzamide;

(d) N-diaminomethylene-2-methyl-4-phenylamino-5-methylsulfonylbenzamide;

(e) N-diaminomethylene-2-methyl-4-(2-pyrimidinylamino)-5-methylsulfonylbenzamide;

(f) N-diaminomethylene-2-methyl-4-(3-chlorophenylamino)-5-methylsulfonylbenzamide;

or a physiologically acceptable salt thereof.

13. A process for the preparation of aminobenzoylguanidine derivatives of formula I according to claim 1, or salts thereof, comprising (a) reacting a compound of formula II

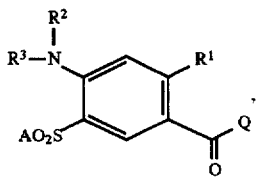

in which

Q is Cl, Br, OA, O—CO—A, O—CO—Ph, OH, a reactive esterified OH group or a leaving group which can readily be substituted nucleophilically, with guanidine, (b) reacting a benzoylguanidine of formula III

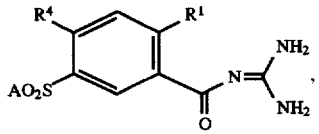

in which

R$^4$ is F, Cl, Br, I or a leaving group, with a compound of the formula IV

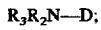

in which D is H, B(OH)$_2$, trialkylsilyl, an alkali metal cation, NH$_4$+ or an easily removable organometallic residue, (c) treating a compound which corresponding to formula I but which contains, instead of one or more hydrogen atoms, one or more reducible groups and/or one or more additional C—C and/or C—N bonds, with a reducing agent; or (d) treating a compound which otherwise corresponds to formula I but which contains, instead of one or more hydrogen atoms, one or more solvolysable groups with a solvolysing agent; or (e) converting a compound of formula I by treatment with an acid into one of its salts.

14. A pharmaceutical composition, comprising an effective amount of at least one compound of formula I according to claim 1, and/or one of its physiologically acceptable salts, and a pharmaceutically acceptable carrier.

15. A method for the treatment or prophylaxis of arrhythmia, angina pectoris or infarction, comprising administering an effective amount of a compound of formula I according to claim 1, or a pharmacologically acceptable salt thereof.

16. A method for the inhibition of the Na$^+$/H$^+$ antiporter, comprising administering an effective amount of a compound of claim 1.

17. A method for the treatment or prophylaxis of hypoxic or ischaemic damage, comprising administering an effective amount of a compound of claim 1.

18. A method for the treatment or prevention of hypertension, or treatment of diseases due to cell proliferation, comprising administering an effective amount of a compound of claim 1.

19. A compound according to claim 1, wherein R$^1$ is C$_{2-6}$-alkyl, CF$_3$, CH$_2$F, CHF$_2$ or C$_2$F$_5$.

20. A compound according to claim 1, wherein R$^1$ is C$_{3-6}$-alkyl, CF$_3$, CH$_2$F, CHF$_2$ or C$_2$F$_5$.

* * * * *